US009201079B2

(12) United States Patent
Soldin

(10) Patent No.: US 9,201,079 B2
(45) Date of Patent: Dec. 1, 2015

(54) METHODS FOR QUANTIFYING VITAMIN D METABOLITES BY MASS SPECTROMETRY

(75) Inventor: Steven J. Soldin, Bethesda, MD (US)

(73) Assignee: Georgetown University, Washington, DC (US)

( * ) Notice: Subject to any disclaimer, the term of this patent is extended or adjusted under 35 U.S.C. 154(b) by 101 days.

(21) Appl. No.: 13/503,963

(22) PCT Filed: Oct. 19, 2010

(86) PCT No.: PCT/US2010/053195
§ 371 (c)(1),
(2), (4) Date: Jun. 7, 2012

(87) PCT Pub. No.: WO2011/056415
PCT Pub. Date: May 12, 2011

(65) Prior Publication Data
US 2012/0244627 A1   Sep. 27, 2012

Related U.S. Application Data

(60) Provisional application No. 61/254,898, filed on Oct. 26, 2009, provisional application No. 61/349,290, filed on May 28, 2010.

(51) Int. Cl.
*G01N 31/22* (2006.01)
*G01N 33/82* (2006.01)
(Continued)

(52) U.S. Cl.
CPC ............ *G01N 33/82* (2013.01); *G01N 33/6848* (2013.01); *H01J 49/00* (2013.01); *Y10T 436/203332* (2015.01)

(58) Field of Classification Search
CPC ............ G01N 33/76; G01N 33/54313; G01N 33/558; G01N 33/74; G01N 33/54366; G01N 33/82; G01N 33/98; G01N 31/22; G01N 1/2813; G01N 33/6848; G01N 33/6803; G01N 21/6408; G01N 31/225; G01N 33/743; B01J 19/0046; B01J 2219/00659; B01J 2219/00585; C07C 233/25; C07C 233/33; C40B 60/14
USPC ........... 436/131, 174, 817; 552/653; 562/575, 562/576, 560, 374, 444
See application file for complete search history.

(56) References Cited

U.S. PATENT DOCUMENTS 7,745,226 B2 * 6/2010 Clarke et al. .................. 436/131
7,972,868 B2 * 7/2011 Holmquist et al. ........... 436/173
(Continued)

FOREIGN PATENT DOCUMENTS

WO   WO-2012/012719 A2   1/2012
WO   WO-2012/087438 A1   6/2012

OTHER PUBLICATIONS

Analysis of Steroid and Vitamin D Glucuronides and Sulfates by Fast Atom Bombardment Mass Spectrometry Ian Jardine, Gale F. Scanlan, Vernon R. Mattox, Rajiv Kumar Biomedical Mass Spectrometry vol. 11, No. 1, 1984.*
(Continued)

*Primary Examiner* — Krishnan S Menon
*Assistant Examiner* — Dwan A Gerido
(74) *Attorney, Agent, or Firm* — Alan W. Steele; Foley Hoag LLP

(57) ABSTRACT

Provided are methods of detecting the presence or amount of a dihydroxyvitamin D metabolite in a sample using mass spectrometry. The methods generally comprise associating an amine with a dihydroxyvitamin D metabolite in a sample, ionizing the adduct, and detecting the amount of the ion to determine the presence or amount of the vitamin D metabolite in the sample.

14 Claims, 3 Drawing Sheets

(51) Int. Cl.
*G01N 33/74* (2006.01)
*G01N 33/68* (2006.01)
*H01J 49/00* (2006.01)

(56) References Cited

U.S. PATENT DOCUMENTS

| | | | |
|---|---|---|---|
| 2004/0132104 | A1 | 7/2004 | Sackrison et al. |
| 2006/0094125 | A1 | 5/2006 | Singh et al. |
| 2006/0228809 | A1* | 10/2006 | Clarke et al. ............... 436/173 |
| 2009/0137056 | A1* | 5/2009 | Holmquist et al. ........... 436/127 |
| 2011/0183429 | A1* | 7/2011 | Dey et al. .................... 436/131 |

OTHER PUBLICATIONS

Mass Fragmentographic Assay for 25-Hydroxyvitamin D in Plasma Without Derivatization: Enhanced Sensitivity for metabolites of Vitamins D2 and D3 After Pre-column Dehydration Ruth D. Coldwell, D.J.H. Trafford, H.L.J Makin Journal of Mass Spectrometry, vol. 30, 348-356, 1995.*

Analysis of Steroid and Vitamin D Glucuronides and Sulfates by Fast Atom Bombardment Mass Spectrometry Ian Jardine, Gale F. Scanlan, Vernon R. Mattox and Rajiv Kumar Biomedical Mass Spectrometry vol. 11 No. 1, 1984.*

Mass Fragmentographic Assay for 25-Hydroxyvitamin D in Plasma Without Derivatization: Enhanced Sensitivity for Metabolites of Vitamins D2 and D3 After Pre-column Dehydration Ruth D. Coldwell, D.J.H. Trafford, and H.L.J. Makin Journal of Mass Spectrometry, vol. 30, 348-356, 1995.*

International Search Report and Written Opinion from parent PCT application PCT/US2010/053195 dated Apr. 14, 2011.

* cited by examiner

Time (minutes)

METHODS FOR QUANTIFYING VITAMIN D METABOLITES BY MASS SPECTROMETRY

RELATED APPLICATIONS

This application is the U.S. national phase of international patent application Ser. No. PCT/US2010/053195, filed Oct. 19, 2010, which claims benefit of priority from U.S. Provisional Application No. 61/349,290, filed May 28, 2010, and U.S. Provisional Application No. 61/254,898, filed Oct. 26, 2009.

BACKGROUND

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxyvitamin $D_3$ (25-hydroxycholecalciferol; calcifediol; $25OHD_3$). Calcifediol is the major form of vitamin $D_3$ in the circulation. Circulating $25OHD_3$ is then converted by the kidney to 1,25-dihydroxyvitamin $D_3$ (calcitriol; $1,25(OH)_2D_3$), which is generally believed to be the metabolite of vitamin $D_3$ with the highest biological activity.

Vitamin $D_2$ is derived from fungal and plant sources. Some over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as vitamin $D_3$, forming the metabolites 25-hydroxyvitamin $D_2$ ($25OHD_2$) and 1,25-dihydroxyvitamin $D_2$ ($1,25(OH)_2D_2$). Vitamin $D_2$ and vitamin $D_3$ have long been assumed to be biologically equivalent in humans, however recent reports suggest that there may be differences in the bioactivity and bioavailability of these two forms of vitamin D (Arras et. al, (2004) J. Clin. Endocrinol. Metab. 89:5387-5391).

Measurement of vitamin D, the inactive vitamin D precursor, is rare in clinical settings and has little diagnostic value. Rather, serum levels of 25-hydroxyvitamin $D_3$ and 25-hydroxyvitamin $D_2$ (total 25-hydroxyvitamin D; "25OHD") are a useful index of vitamin D nutritional status and the efficacy of certain vitamin D analogs. Therefore, the measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1,25(OH)_2D$ is also used in clinical settings. For example certain disease states such as kidney failure can be diagnosed by reduced levels of circulating $1,25(OH)_2D$ and elevated levels of $1,25(OH)_22D$ may be indicative of excess parathyroid hormone or may be indicative of certain diseases such as sarcoidosis or certain types of lymphoma.

Detection of vitamin D metabolites has been accomplished by radioimmunoassay with antibodies co-specific for 25-hydroxyvitamin $D_3$ and 25-hydroxyvitamin $D_2$. Because the current immunologically-based assays do not separately resolve 25-hydroxyvitamin $D_3$ and 25-hydroxyvitamin $D_2$, the source of a deficiency in vitamin D nutrition cannot be determined without resorting to other tests. More recently, reports have been published that disclose methods for detecting specific vitamin D metabolites using mass spectrometry. For example Yeung B. et al., J. Chromatogr. 1993, 645(1): 115-23; Higashi T, et al., Steroids. 2000, 65(5):281-94; Higashi T, et al., Biol Pharm Bull. 2001, 24(7):738-43; and Higashi T, et al., J Pharm Biomed Anal. 2002, 29(5):947-55 disclose methods for detecting various vitamin D metabolites using liquid chromatography and mass spectrometry. These methods require that the metabolites be derivatized prior to detection by mass-spectrometry. Methods to detect underivatized $1,25(OH)_2D_3$ by liquid chromatography/mass-spectrometry are disclosed in Kissmeyer and Sonne, J Chromatogr A. 2001, 935(1-2):93-103. Detection of vitamin D metabolites by mass spectrometry is also discussed in U.S. Patent Application Publication No. 2009/0137056 to B. Holmquist et al.

SUMMARY OF THE INVENTION

One aspect of the present invention provides methods for detecting by mass spectrometry the presence or amount of a dihydroxyvitamin D metabolite in a sample. In certain embodiments, methods are provided for determining by mass spectrometry the presence or amount of one or more dihydroxyvitamin D metabolites, that include: (a) combining a first sample with a first amount of an amine or an alkali metal ion, thereby forming a second sample comprising non-covalent adducts comprising the amine or the alkali metal ion and the dihydroxyvitamin D metabolite; (b) injecting the second sample into a mass spectrometer, thereby generating a plurality of ions from the non-covalent adducts; and (c) detecting and quantifying one or more ions.

DETAILED DESCRIPTION OF THE INVENTION

Figure 1:
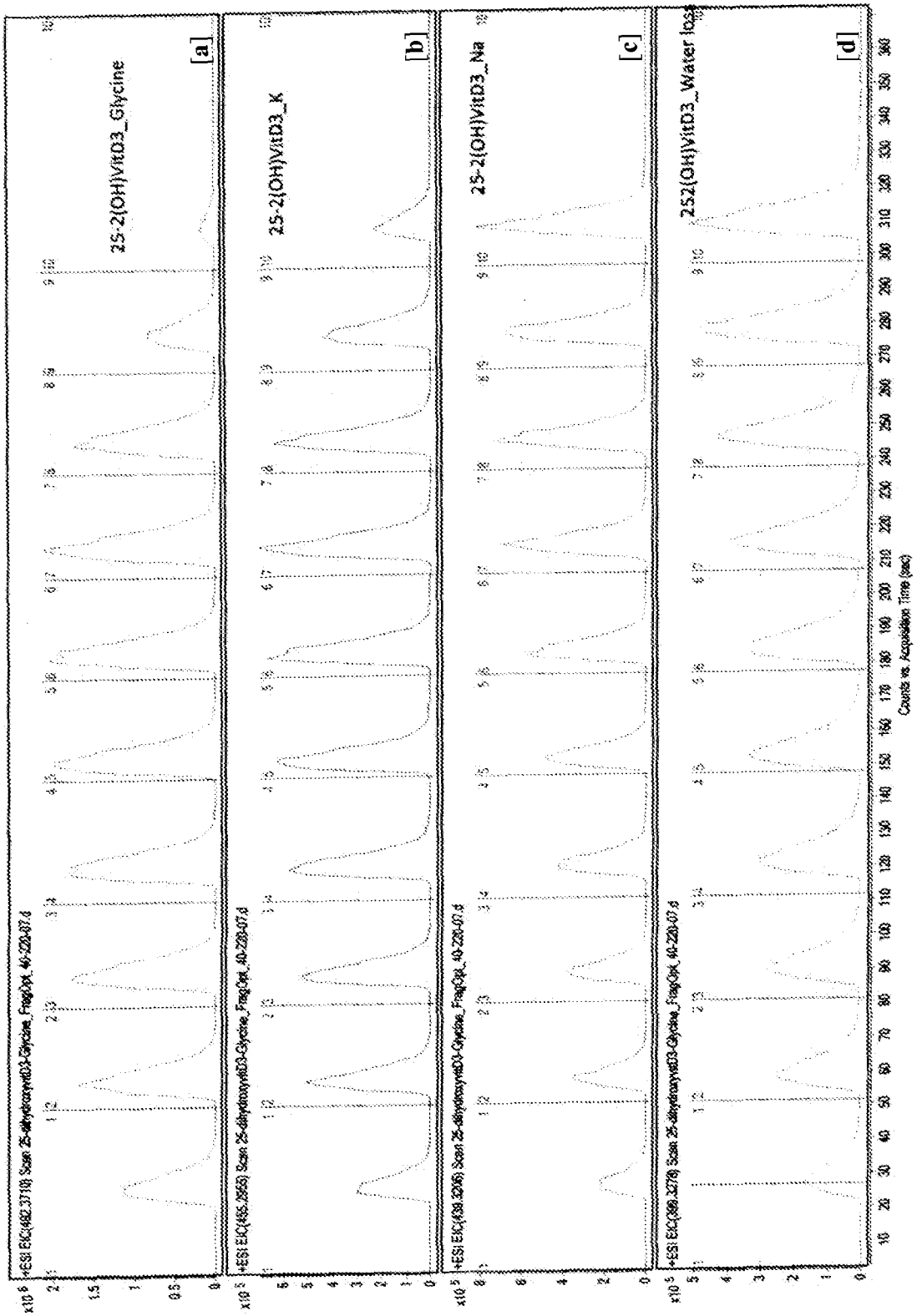
FIG. 1 depicts chromatograms of the 1,25-dihydroxyvitamin $D_3$ adduct with [a] glycine ion, [b] potassium ion (K+) and [c] sodium ion ($Na^+$). Also shown is [d] a chromatogram of protonated 1,25-dihydroxyvitamin $D_3$ with the loss of one equivalent of water (water loss).
Figure 2:
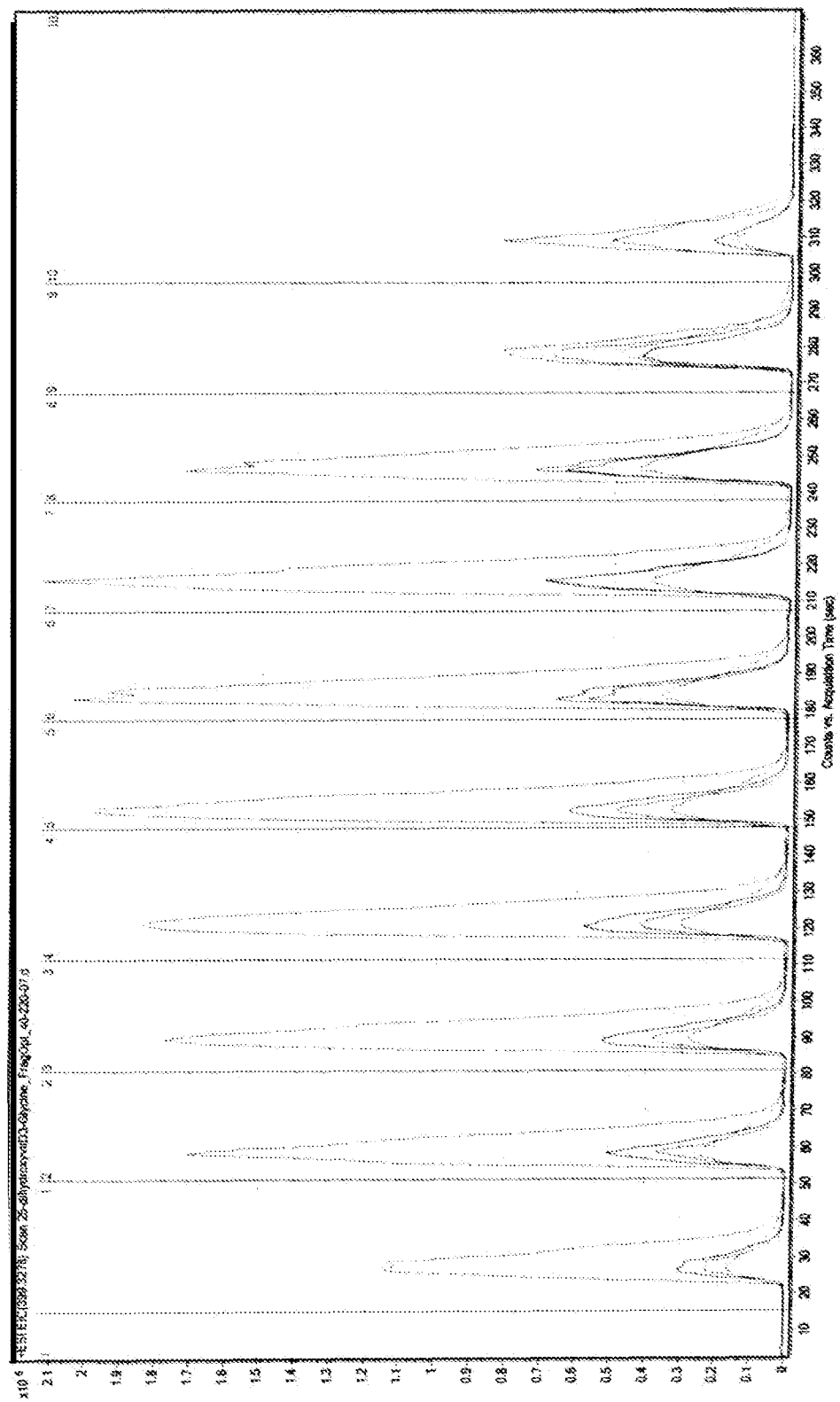
FIG. 2 shows all of the chromatograms of FIG. 1 on one graph.

Methods are described using mass spectrometry for detecting and quantifying dihydroxyvitamin D metabolites in a test sample. In certain aspects, the method involves forming an amine/dihydroxyvitamin D metabolite adduct or an alkali metal/dihydroxyvitamin D metabolite adduct, ionizing the adduct, detecting the ion(s) by mass spectrometry, and relating the presence or amount of the ion(s) to the presence or amount of the dihydroxyvitamin D metabolite(s) in the sample. Certain embodiments are particularly well suited for application in large clinical laboratories. Methods of detecting and quantifying dihydroxyvitamin D metabolites are provided that have enhanced specificity and/or are accomplished in less time and with less sample preparation than required in other dihydroxyvitamin D metabolite assays.

Definitions

All definitions, as defined and used herein, should be understood to control over dictionary definitions, definitions in documents incorporated by reference, and/or ordinary meanings of the defined terms.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, an "adduct" is a species formed by the union of an amine and a dihydroxyvitamin D metabolites held together by one or more covalent and/or non-covalent bonds.

The term "about," as used herein in reference to quantitative measurements, refers to the indicated value plus or minus 10%.

As used herein, the term "dihydroxyvitamin D metabolite" refers to any dihydroxylated vitamin D species that may be found in the circulation of an animal which is formed by a biosynthetic or metabolic pathway for vitamin D or a synthetic vitamin D analog. In certain embodiments the dihydroxyvitamin D metabolite is hydroxylated at the 1 and 25 position. In certain embodiments the vitamin D metabolite is 1α,25-dihydroxyvitamin $D_3$ (1α,25(OH)$_2$$D_3$) or 1α,25-dihydroxyvitamin $D_2$ (1α,25(OH)$_2$$D_2$). In certain embodiments the dihydroxyvitamin D metabolites are naturally present in a body fluid of a mammal (such as a human). In certain embodiments the methods as described herein selectively detect 1α,25-dihydroxyvitamin $D_3$ (1α,25(OH)$_2$$D_3$) and/or 1α,25-dihydroxyvitamin $D_2$ (1α,25(OH)$_2$$D_2$).

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include Cookson-type reagents (e.g., 4-substituted 1,2,4-triazoline-3,5-diones; TAD); isothiocyanate groups, dinitrofluorophenyl groups, nitrophenoxycarbonyl groups, and/or phthalaldehyde groups. In certain embodiments, derivitization is performed using methods such as those disclosed in, for example, Vreeken, et al., Biol. Mass Spec. 22:621-632; Yeung B, et al., J. Chromatogr. 1993, 645(1):115-23; Higashi T, et al., Biol Pharm Bull. 2001, 24(7):738-43; or Higashi T, et al., J Pharm Biomed Anal. 2002, 29(5):947-55. In certain embodiments the derivatizing agents are Cookson-type reagents. Exemplary derivatizing reagents include 4-phenyl-1,2,4-triazoline-3,5-dione (PTAD); 4'-carboxyphenyl-TAD; 4-[4-(6-methoxy-2-benzoxazolyl)phenyl]-1,2,4-triazoline-3,5-dione (MBOTAD); 4-[2-(6,7-dimethoxy-4-methyl-3-oxo-3,4-dihydroquinoxalyl)ethyl]-1,2,4-triazoline-3,5-dione (DMEQTAD); 4-nitrophenyl-TAD; 4-pentafluorophenyl-TAD; 4-ferrocenylethyl-TAD; 4-quarternaryamine-TAD; and the like. In certain embodiments derivitization is performed prior to chromatography; however in other embodiments derivitization is performed after chromatography, for example using methods similar to those described in Vreeken, et al., Biol. Mass Spec. 22:621-632. In certain embodiments of the methods disclosed herein, the dihydroxyvitamin D metabolite(s) are not derivatized prior to mass spectrometry.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase As used herein, "mass spectrometry" (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;"6,124,137, entitled "Surface-Enhanced Photolabile Attachment And Release For Desorption And Detection Of Analytes;" Wright et al., Prostate Cancer and Prostatic Diseases 2:264-76 (1999); and Merchant and Weinberger, Electrophoresis 21:1164-67 (2000).

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g., ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "arylalkyl" as used herein means an aryl group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene," is art-recognized, and as used herein pertains to a bidentate moiety obtained by removing two hydrogen atoms of an alkyl group, as defined above.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein means —NHC(═O)—, wherein the amido group is bound to the parent molecular moiety through the nitrogen. Examples of amido include alkylamido such as $CH_3C(═O)N(H)$— and $CH_3CH_2C(═O)N(H)$—.

The term "amino" as used herein refers to radicals of both unsubstituted and substituted amines appended to the parent molecular moiety through a nitrogen atom. The additional groups appended to the nitrogen are independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "aryl," as used herein means a phenyl group or a naphthyl group. The aryl groups of the present invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkoxy" or "arylalkyloxy" as used herein means an arylalkyl group, as defined herein, appended to the parent molecular moiety through an oxygen. The term "heteroarylalkoxy" as used herein means an heteroarylalkyl group, as defined herein, appended to the parent molecular moiety through an oxygen.

The term "arylalkylthio" as used herein means an arylalkyl group, as defined herein, appended to the parent molecular moiety through an sulfur. The term "heteroarylalkylthio" as used herein means an heteroarylalkyl group, as defined herein, appended to the parent molecular moiety through an sulfur.

The term "arylalkenyl" as used herein means an aryl group, as defined herein, appended to the parent molecular moiety through an alkenyl group. A representative example is phenylethylenyl.

The term "arylalkynyl" as used herein means an aryl group, as defined herein, appended to the parent molecular moiety through an alkynyl group. A representative example is phenylethynyl.

The term "arylcarbonyl" as used herein means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein means an arylcarbonyl group, as defined herein, bound to the parent molecule through an alkyl group, as defined herein.

The term "arylcarbonylalkoxy" as used herein means an arylcarbonylalkyl group, as defined herein, bound to the parent molecule through an oxygen.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen.

The term "carbonyl" as used herein means a —C(═O)— group.

The term "carboxy" as used herein means a —CO$_2$H group.

The term "cycloalkyl" as used herein means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein means a cycloalkyl group, as defined herein, appended to the parent molecular moiety through an oxygen.

The term "cyano" as used herein means a —CN group.

The term "formyl" as used herein means a —C(═O)H group.

The term "halo" or "halogen" means —Cl, —Br, —I or —F.

The term "haloalkoxy" as used herein means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein means an —OH group.

The term "hydroxyalkyl" as used herein means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein means a —SH group.

The term "nitro" as used herein means a —NO$_2$ group.

The term "phosphinyl" as used herein includes derivatives of the H$_3$P— group, wherein the hydrogens are independently replaced with alkyl, adamantyl, fluoroalkyl, cycloalkyl, aryl, heteroaryl, heterocycyl, aryloxy, or heteroaryloxy groups.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used herein, "amine" refers to organic compounds and functional groups that contain a basic nitrogen atom with a lone electron pair. Amines are derivatives of ammonia, wherein one or more hydrogen atoms have been replaced by a substituent such as, for example, an alkyl or aryl group. As used herein, the term "amine" also includes amino acids.

The term "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups.

The term "amino acid" further includes analogues, derivatives, and congeners of any specific amino acid referred to herein, as well as C-terminal or N-terminal protected amino acid derivatives (e.g., modified with an N-terminal or C-terminal protecting group).

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature.

Examples of non-naturally occurring amino acids include, but are not limited to, D-amino acids (i.e., an amino acid of an opposite chirality to the naturally occurring form), N-α-methyl amino acids, C-α-methyl amino acids, β-methyl amino acids, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), D- or L-phenylglycine, D- or L-2-naphthylalanine (2-Nal), 1,2,3,4-tetrahydroisoquinoline-3-carboxylic acid (Tic), D- or L-2-thienylalanine (Thi), D- or L-3-thienylalanine, D- or L-1-, 2-, 3- or 4-pyrenylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har). Other examples include D- or L-2-indole (alkyl)alanines and D- or L-alkylalanines, wherein alkyl is substituted or unsubstituted methyl, ethyl, propyl, hexyl, butyl, pentyl, isopropyl, iso-butyl, or iso-pentyl, and phosphono- or sulfated (e.g., —SO$_3$H) non-carboxylate amino acids, and protected forms thereof.

Other examples of non-naturally occurring amino acids include 3-(2-chlorophenyl)-alanine, 3-chloro-phenylalanine, 4-chloro-phenylalanine, 2-fluoro-phenylalanine, 3-fluoro-phenylalanine, 4-fluoro-phenylalanine, 2-bromo-phenylalanine, 3-bromo-phenylalanine, 4-bromo-phenylalanine, homophenylalanine, 2-methyl-phenylalanine, 3-methyl-phenylalanine, 4-methyl-phenylalanine, 2,4-dimethyl-phenylalanine, 2-nitro-phenylalanine, 3-nitro-phenylalanine, 4-nitro-phenylalanine, 2,4-dinitro-phenylalanine, 1,2,3,4-Tetrahydroisoquinoline-3-carboxylic acid, 1,2,3,4-tetrahydronorharman-3-carboxylic acid, 1-naphthylalanine, 2-naphthylalanine, pentafluorophenylalanine, 2,4-dichloro-phenylalanine, 3,4-dichloro-phenylalanine, 3,4-difluoro-phenylalanine, 3,5-difluoro-phenylalanine, 2,4,5-trifluoro-phenylalanine, 2-trifluoromethyl-phenylalanine, 3-trifluoromethyl-phenylalanine, 4-trifluoromethyl-phenylalanine, 2-cyano-phenyalanine, 3-cyano-phenyalanine, 4-cyano-phenyalanine, 2-iodo-phenyalanine, 3-iodo-phenyalanine, 4-iodo-phenyalanine, 4-methoxyphenylalanine, 2-aminomethyl-phenylalanine, 3-aminomethyl-phenylalanine, 4-aminomethyl-phenylalanine, 2-carbamoyl-phenylalanine, 3-carbamoyl-phenylalanine, 4-carbamoyl-phenylalanine, m-tyrosine, 4-amino-phenylalanine, styrylalanine, 2-amino-5-phenyl-pentanoic acid, 9-anthrylalanine, 4-tert-butyl-phenylalanine, 3,3-diphenylalanine, 4,4'-diphenylalanine, benzoylphenylalanine, α-methyl-phenylalanine, α-methyl-4-fluoro-phenylalanine, 4-thiazolylalanine, 3-benzothienylalanine, 2-thienylalanine, 2-(5-bromothienyl)-alanine, 3-thienylalanine, 2-furylalanine, 2-pyridylalanine, 3-pyridylalanine, 4-pyridylalanine, 2,3-diaminopropionic acid, 2,4-diaminobutyric acid, allylglycine, 2-amino-4-bromo-4-pentenoic acid, propargylglycine, 4-aminocyclopent-2-enecarboxylic acid, 3-aminocyclopentanecarboxylic acid, 7-amino-heptanoic acid, dipropylglycine, pipecolic acid, azetidine-3-carboxylic acid, cyclopropylglycine, cyclopropylalanine, 2-methoxy-phenylglycine, 2-thienylglycine, 3-thienylglycine, α-benzyl-proline, α-(2-fluoro-benzyl)-proline, α-(3-fluoro-benzyl)-proline, α-(4-fluoro-benzyl)-proline, α-(2-chloro-benzyl)-proline, α-(3-chloro-benzyl)-proline, α-(4-chloro-benzyl)-proline, α-(2-bromo-benzyl)-proline, α-(3-bromo-benzyl)-proline, α-(4-bromo-benzyl)-proline, α-phenethyl-proline, α-(2-methyl-benzyl)-proline, α-(3-methyl-benzyl)-proline, α-(4-methyl-benzyl)-proline, α-(2-nitro-benzyl)-proline, α-(3-nitro-benzyl)-proline, α-(4-nitro-benzyl)-proline, α-(1-naphthalenylmethyl)-proline, α-(2-naphthalenylmethyl)-proline, α-(2,4-dichloro-benzyl)-proline, α-(3,4-dichloro-benzyl)-proline, α-(3,4-difluoro-benzyl)-proline, α-(2-trifluoromethyl-benzyl)-proline, α-(3-trifluoromethyl-benzyl)-proline, α-(4-trifluoromethyl-benzyl)-proline, α-(2-cyano-benzyl)-proline, α-(3-cyano-benzyl)-proline, α-(4-cyano-benzyl)-proline, α-(2-iodo-benzyl)-proline, α-(3-iodo-benzyl)-proline, α-(4-iodo-benzyl)-proline, α-(3-phenyl-allyl)-proline, α-(3-phenyl-propyl)-proline, α-(4-tert-butyl-benzyl)-proline, α-benzhydryl-proline, α-(4-biphenylmethyl)-proline, α-(4-thiazolylmethyl)-proline, α-(3-benzo[b]thiophenylmethyl)-proline, α-(2-thiophenylmethyl)-proline, α-(5-bromo-2-thiophenylmethyl)-proline, α-(3-thiophenylmethyl)-proline, α-(2-furanylmethyl)-proline, α-(2-pyridinylmethyl)-proline, α-(3-pyridinylmethyl)-proline, α-(4-pyridinylmethyl)-proline, α-allyl-proline, α-propynyl-proline, γ-benzyl-proline, γ-(2-fluoro-benzyl)-proline, γ-(3-fluoro-benzyl)-proline, γ-(4-fluoro-benzyl)-proline, γ-(2-chloro-benzyl)-proline, γ-(3-chloro-benzyl)-proline, γ-(4-chloro-benzyl)-proline, γ-(2-bromo-benzyl)-proline, γ-(3-bromo-benzyl)-proline, γ-(4-bromo-benzyl)-proline, γ-(2-methyl-benzyl)-proline, γ-(3-methyl-benzyl)-proline, γ-(4-methyl-benzyl)-proline, γ-(2-nitro-benzyl)-proline, γ-(3-nitro-benzyl)-proline, γ-(4-nitro-benzyl)-proline, γ-(1-naphthalenylmethyl)-proline, γ-(2-naphthalenylmethyl)-proline, γ-(2,4-dichloro-benzyl)- proline, γ-(3,4-dichloro-benzyl)-proline, γ-(3,4-difluoro-benzyl)-proline, γ-(2-trifluoromethyl-benzyl)-proline, γ-(3-trifluoromethyl-benzyl)-proline, γ-(4-trifluoromethyl-benzyl)-proline, γ-(2-cyano-benzyl)-proline, γ-(3-cyano-benzyl)-proline, γ-(4-cyano-benzyl)-proline, γ-(2-iodo-benzyl)-proline, γ-(3-iodo-benzyl)-proline, γ-(4-iodo-benzyl)-proline, γ-(3-phenyl-allyl-benzyl)-proline, γ-(3-phenyl-propyl-benzyl)-proline, γ-(4-tert-butyl-benzyl)-proline, γ-benzhydryl-proline, γ-(4-biphenylmethyl)-proline, γ-(4-thiazolylmethyl)-proline, γ-(3-benzothioienylmethyl)-proline, γ-(2-thienylmethyl)-proline, γ-(3-thienylmethyl)-proline, γ-(2-furanylmethyl)-proline, γ-(2-pyridinylmethyl)-proline, γ-(3-pyridinylmethyl)-proline, γ-(4-pyridinylmethyl)-proline, γ-allyl-proline, γ-propynyl-proline, trans-4-phenyl-pyrrolidine-3-carboxylic acid, trans-4-(2-fluoro-phenyl)-pyrrolidine-3-carboxylic acid, trans-4-(3-fluoro-phenyl)-pyrrolidine-3-carboxylic acid, trans-4-(4-fluoro-phenyl)-pyrrolidine-3-carboxylic acid, trans-4-(2-chloro-phenyl)-pyrrolidine-3-carboxylic acid, trans-4-(3-chloro-phenyl)-pyrrolidine-3-carboxylic acid, trans-4-(4-chloro-phenyl)-pyrrolidine-3-carboxylic acid, trans-4-(2-bromo-phenyl)-pyrrolidine-3-carboxylic acid, trans-4-(3-bromo-phenyl)-pyrrolidine-3-carboxylic acid, trans-4-(4-bromo-phenyl)-pyrrolidine-3-carboxylic acid, trans-4-(2-methyl-phenyl)-pyrrolidine-3-carboxylic acid, trans-4-(3-methyl-phenyl)-pyrrolidine-3-carboxylic acid, trans-4-(4-methyl-phenyl)-pyrrolidine-3-carboxylic acid, trans-4-(2-nitro-phenyl)-pyrrolidine-3-carboxylic acid, trans-4-(3-nitro-phenyl)-pyrrolidine-3-carboxylic acid, trans-4-(4-nitro-phenyl)-pyrrolidine-3-carboxylic acid, trans-4-(1-naphthyl)-pyrrolidine-3-carboxylic acid, trans-4-(2-naphthyl)-pyrrolidine-3-carboxylic acid, trans-4-(2,5-dichloro-phenyl)-pyrrolidine-3-carboxylic acid, trans-4-(2,3-dichloro-phenyl)-pyrrolidine-3-carboxylic acid, trans-4-(2-trifluoromethyl-phenyl)-pyrrolidine-3-carboxylic acid, trans-4-(3-trifluoromethyl-phenyl)-pyrrolidine-3-carboxylic acid, trans-4-(4-trifluoromethyl-phenyl)-pyrrolidine-3-carboxylic acid, trans-4-(2-cyano-phenyl)-pyrrolidine-3-carboxylic acid, trans-4-(3-cyano-phenyl)-pyrrolidine-3-carboxylic acid, trans-4-(4-cyano-phenyl)-pyrrolidine-3-carboxylic acid, trans-4-(2-methoxy-phenyl)-pyrrolidine-3-carboxylic acid, trans-4-(3-methoxy-phenyl)-pyrrolidine-3-carboxylic acid, trans-4-(4-methoxy-phenyl)-pyrrolidine-3-carboxylic acid, trans-4-(2-hydroxy-phenyl)-pyrrolidine-3-carboxylic acid, trans-4-(3-hydroxy-phenyl)-pyrrolidine-3-carboxylic acid, trans-4-(4-hydroxy-phenyl)-pyrrolidine-3-carboxylic acid, trans-4(2,3-dimethoxy-phenyl)-pyrrolidine-3-carboxylic acid, trans-4(3,4-dimethoxy-phenyl)-pyrrolidine-3-carboxylic acid, trans-4-(3,5-dimethoxy-phenyl)-pyrrolidine-3-carboxylic acid, trans-4-(2-pyridinyl)-pyrrolidine-3-carboxylic acid, trans-4(3-pyridinyl)-pyrrolidine-3-carboxylic acid, trans-4-(6-methoxy-3-pyridinyl)-pyrrolidine-3-carboxylic acid, trans-4(4-pyridinyl)-pyrrolidine-3-carboxylic acid, trans-4-(2-thienyl)-pyrrolidine-3-carboxylic acid, trans-4-(3-thienyl)-pyrrolidine-3-carboxylic acid, trans-4-(2-furanyl)-pyrrolidine-3-carboxylic acid, trans-4-isopropyl-pyrrolidine-3-carboxylic acid, 4-phosphonomethyl-phenylalanine, benzyl-phosphothreonine, (1'-amino-2-phenyl-ethyl)oxirane, (1'-amino-2-cyclohexyl-ethyl)oxirane, (1'-amino-2-[3-bromo-phenyl]ethyl)oxirane, (1'-amino-2-[4-(benzyloxy)phenyl]ethyl)oxirane, (1'-amino-2-[3,5-difluoro-phenyl]ethyl)oxirane, (1'-amino-2-[4-carbamoyl-phenyl]ethyl)oxirane, (1'-amino-2-[benzyloxy-ethyl])oxirane, (1'-amino-2-[4-nitro-phenyl]ethyl)oxirane, (1'-amino-3-phenyl-propyl)oxirane, (1'-amino-3-phenyl-propyl)oxirane, and protected forms thereof.

"Amino acid" also includes N-terminal and C-terminal protected amino acids. The term "amino-protecting group" or "N-terminal protecting group" refers to those groups intended to protect the α-N-terminal of an amino acid. Commonly used N-protecting groups are disclosed in Greene, *Protective Groups In Organic Synthesis*, (John Wiley & Sons, New York (1981)), which is hereby incorporated by reference. α-N-Protecting groups comprise, for example, lower alkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like. Still other examples include theyl, succinyl, methoxysuccinyl, subery, adipyl, azelayl, dansyl, benzyloxycarbonyl, methoxyazelaly, methoxyadipyl, methoxysuberyl, and 2,4-dinitrophenyl.

The term "carboxy protecting group" or "C-terminal protecting group" refers to a carboxylic acid protecting ester or amide group. Carboxy protecting groups are disclosed in Greene, *Protective Groups in Organic Synthesis* pp. 152-186 (1981), which is hereby incorporated by reference. Representative carboxy protecting groups are $C_1$-$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like. Representative amide carboxy protecting groups are aminocarbonyl and loweralkylaminocarbonyl groups. For example, aspartic acid may be protected at the α-C-terminal by an acid labile group (e.g., t-butyl) and protected at the β-C-terminal by a hydrogenation labile group (e.g., benzyl) then deprotected selectively during synthesis. As mentioned above, the protected carboxy group may also be a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

Selected Amines

As noted above, certain aspects of the invention involve forming an adduct between an amine and a dihydroxyvitamin D metabolite. Non-limiting examples of amines which may be used to form such adducts are provided below.

In certain embodiments, the amine used to form the adduct is represented by formula I:

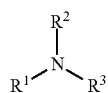

I wherein, $R^1$ and $R^2$ are independently selected from the group consisting of hydrogen, alkyl, cycloalkyl, alkenyl, alkynyl, heterocyclyl, aryl, heteroaryl, heterocyclylalkyl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, optionally substituted with 1-5 substituents independently selected from the group consisting of alkyl, cycloalkyl, alkenyl, alkynyl, heterocyclyl, heterocyclylalkyl, aryl, heteroaryl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, alkoxy, alkenyloxy, alkynyloxy, aryloxy, heteroaryloxy, aralkyloxy, heteroaralkyloxy, alkoxysulfonyl, alkylsulfonyl, alkylthio, amido, amino, carboxy, cyano, formyl, halo, haloalkoxy, haloalkyl, hydroxyl, hydroxyalkyl, mercapto, nitro, phosphinyl, silyl and silyloxy; or $R^1$ and $R^2$ taken together with the nitrogen to which they are bound form a heterocycle; and $R^3$ is selected from the group consisting of hydrogen, alkyl, cycloalkyl, alkenyl, alkynyl, heterocyclyl, aryl, heteroaryl, heterocyclylalkyl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, optionally substituted with 1-5 substituents independently selected from the group consisting of alkyl, cycloalkyl, alkenyl, alkynyl, heterocyclyl, heterocyclylalkyl, aryl, heteroaryl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, alkoxy, alkenyloxy, alkynyloxy, aryloxy, heteroaryloxy, aralkyloxy, heteroaralkyloxy, alkoxysulfonyl, alkylsulfonyl, alkylthio, amido, amino, carboxy, cyano, formyl, halo, haloalkoxy, haloalkyl, hydroxyl, hydroxyalkyl, mercapto, nitro, phosphinyl, silyl and silyloxy;

provided that if $R^1$ is hydrogen and $R^2$ is hydrogen, $R^3$ is not hydrogen.

In certain embodiments, the amine used to form the adduct is represented by formula I, wherein $R^1$ is hydrogen.

In certain embodiments, the amine used to form the adduct is represented by formula I, wherein $R^2$ is hydrogen.

In certain embodiments, the amine used to form the adduct is represented by formula I, wherein $R^1$ and $R^2$ are hydrogen.

In certain embodiments, the amine used to form the adduct is represented by formula II:

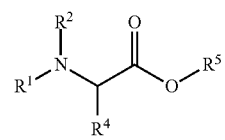

II wherein, $R^1$ and $R^2$ are independently selected from the group consisting of hydrogen, alkyl, cycloalkyl, alkenyl, alkynyl, heterocyclyl, aryl, heteroaryl, heterocyclylalkyl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, optionally substituted with 1-5 substituents independently selected from the group consisting of alkyl, cycloalkyl, alkenyl, alkynyl, heterocyclyl, heterocyclylalkyl, aryl, heteroaryl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, alkoxy, alkenyloxy, alkynyloxy, aryloxy, heteroaryloxy, aralkyloxy, heteroaralkyloxy, alkoxysulfonyl, alkylsulfonyl, alkylthio, amido, amino, carboxy, cyano, formyl, halo, haloalkoxy, haloalkyl, hydroxyl, hydroxyalkyl, mercapto, nitro, phosphinyl, silyl and silyloxy; or $R^1$ and $R^2$ taken together with the nitrogen to which they are bound form a heterocycle;

$R^4$ is selected from the group consisting of hydrogen, alkyl, cycloalkyl, alkenyl, alkynyl, heterocyclyl, aryl, heteroaryl, heterocyclylalkyl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, optionally substituted with 1-5 substituents independently selected from the group consisting of alkyl, cycloalkyl, alkenyl, alkynyl, heterocyclyl, heterocyclylalkyl, aryl, heteroaryl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, alkoxy, alkenyloxy, alkynyloxy, aryloxy, heteroaryloxy, aralkyloxy, heteroaralkyloxy, alkoxysulfonyl, alkylsulfonyl, alkylthio, amido, amino, carboxy, cyano, formyl, halo, haloalkoxy, haloalkyl, hydroxyl, hydroxyalkyl, mercapto, nitro, phosphinyl, silyl and silyloxy; and $R^5$ is selected from the group consisting of hydrogen, alkyl, cycloalkyl, alkenyl, alkynyl, heterocyclyl, aryl, heteroaryl, heterocyclylalkyl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, optionally substituted with 1-5 substituents independently selected from the group consisting of alkyl, cycloalkyl, alkenyl, alkynyl, heterocyclyl, heterocyclylalkyl, aryl, heteroaryl, aralkyl, heteroaralkyl, formyl, carboxy, alkylcarbonyl, cycloalkylcarbonyl, alkenylcarbonyl, alkynylcarbonyl, heterocyclylcarbonyl, heterocyclylalkylcarbonyl, arylcarbonyl, heteroarylcarbonyl, aralkylcarbonyl, heteroaralkylcarbonyl, alkyloxycarbonyl, cycloalkyloxycarbonyl, alkenyloxycarbonyl, alkynyloxycarbonyl, heterocyclyloxycarbonyl, heterocyclylalkoxycarbonyl, aryloxycarbonyl, heteroaryloxycarbonyl, aralkyloxycarbonyl, heteroaralkyloxycarbonyl, aminocarbonyl, alkoxy, alkenyloxy, alkynyloxy, aryloxy, heteroaryloxy, aralkyloxy, heteroaralkyloxy, alkoxysulfonyl, alkylsulfonyl, alkylthio, amido, amino, carboxy, cyano, formyl, halo, haloalkoxy, haloalkyl, hydroxyl, hydroxyalkyl, mercapto, nitro, phosphinyl, silyl and silyloxy.

In certain embodiments, the amine used to form the adduct is represented by formula II, wherein $R^1$ is hydrogen.

In certain embodiments, the amine used to form the adduct is represented by formula II, wherein $R^2$ is hydrogen.

In certain embodiments, the amine used to form the adduct is represented by formula II, wherein $R^1$ and $R^2$ are hydrogen.

In certain embodiments, the amine used to form the adduct is represented by formula II, wherein $R^5$ is hydrogen.

In certain embodiments, the amine used to form the adduct is represented by formula II, wherein $R^1$, $R^2$ and $R^5$ are hydrogen.

In certain embodiments, the amine used to form the adduct is represented by formula II, wherein the amine is alanine (Ala), arginine (Arg), asparagine (Asn), aspartic acid (Asp), cysteine (Cys), glutamic acid (Glu), glutamine (Gln), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val).

In certain embodiments, the amine used to form the adduct is represented by formula II, wherein the amine is glycine, alanine, serine, or arginine.

In certain embodiments, the amine used to form the adduct is represented by formula II, wherein $R^4$ is 4-(aryloxyl) aralkyl.

In certain embodiments, the amine used to form the adduct is represented by formula II, wherein $R^1$, $R^2$ and $R^5$ are hydrogen; and $R^4$ is 4-(aryloxyl)aralkyl.

In certain embodiments, the amine used to form the adduct is represented by formula II, wherein $R^4$ is 4-(aryloxyl) aralkyl substituted with 1-4 substituents independently selected from the group consisting of halo and hydroxy.

In certain embodiments, the amine used to form the adduct is represented by formula II, wherein $R^1$, $R^2$ and $R^5$ are hydrogen; and $R^4$ is 4-(aryloxyl)aralkyl substituted with 1-4 substituents independently selected from the group consisting of halo and hydroxy.

In certain embodiments, the amine used to form the adduct is represented by formula II, wherein the amine is thyroxine, triiodothyronine, diiodothyronine, or iodothyronine.

Selected Adducts

One aspect of the invention relates to an adduct comprising an amine or an alkali metal ion and a dihydroxyvitamin D metabolite.

In certain embodiments, the present invention relates to any one of the aforementioned adducts, wherein the adduct comprises an amine. In certain embodiments, the present invention relates to any one of the aforementioned adducts, wherein the amine is an amine of formula I or formula II. In certain embodiments, the present invention relates to any one of the aforementioned adducts, wherein the amine is glycine, alanine, serine, arginine, thyroxine, triiodothyronine, diiodothyronine, or iodothyronine.

In certain embodiments, the present invention relates to any one of the aforementioned adducts, wherein the adduct comprises an alkali metal ion. In certain embodiments, the present invention relates to any one of the aforementioned adducts, wherein the alkali metal ion is a sodium ion. In certain embodiments, the present invention relates to any one of the aforementioned adducts, wherein the alkali metal ion is a potassium ion. In certain embodiments, the present invention relates to any one of the aforementioned adducts, wherein the alkali metal ion is a lithium ion.

In certain embodiments, the present invention relates to any one of the aforementioned adducts, wherein the dihydroxyvitamin D metabolite is 1,25-dihydroxyvitamin $D_2$ or 1,25-dihydroxyvitamin $D_3$. In certain embodiments, the present invention relates to any one of the aforementioned adducts, wherein the dihydroxyvitamin D metabolite is 1,25-dihydroxyvitamin $D_2$. In certain embodiments, the present invention relates to any one of the aforementioned adducts, wherein the dihydroxyvitamin D metabolite is 1,25-dihydroxyvitamin $D_3$.

In certain embodiments, the present invention relates to any one of the aforementioned adducts, wherein the adduct is a non-covalent adduct.

Test Samples

Suitable test samples include any test sample that may contain the analyte of interest. For example, samples obtained during the manufacture of an analyte can be analyzed to determine the composition and yield of the manufacturing process. In some embodiments, a sample is a biological sample; that is, a sample obtained from any biological source, such as an animal, a cell culture, an organ culture, etc. In certain embodiments, samples are obtained from a mammalian animal, such as a dog, cat, horse, etc. Exemplary mammalian animals are primates, most preferably humans. Exemplary samples include blood, plasma, serum, hair, muscle, urine, saliva, tear, cerebrospinal fluid, or other tissue sample. Such samples may be obtained, for example, from a patient; that is, a living person presenting oneself in a clinical setting for diagnosis, prognosis, or treatment of a disease or condition. The test sample may be obtained from a patient, for example, blood serum.

Sample Preparation for Mass Spectrometry

Methods may be used prior to mass spectrometry to enrich dihydroxyvitamin D metabolites relative to other components in the sample, or to increase the concentration of the dihydroxyvitamin D metabolites in the sample. Such methods include, for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, delipidization, dilution, combinations thereof and the like. Protein precipitation is one method of preparing a liquid biological sample, such as serum or plasma, for chromatography. Such protein prescription methods are well known in the art, for example, Polson et al., Journal of Chromatography B 785:263-275 (2003), describes protein precipitation methods suitable for use in the methods of the invention. Protein precipitation may be used to remove most of the protein from the sample leaving dihydroxyvitamin D metabolites soluble in the supernatant. The samples can be centrifuged to separate the liquid supernatant from the precipitated proteins. The resultant supernatant can then be applied to liquid chromatography and subsequent mass spectrometry analysis. In one embodiment of the invention, the protein precipitation involves adding one volume of the liquid sample (e.g., plasma) to about four volumes of methanol. In another embodiment, the protein precipitation involves adding two volumes of liquid sample (e.g., plasma) to about three volumes of methanol. In certain embodiments of protein precipitation, the methanol solution contains an internal standard and/or the adduct. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

Liquid Chromatography

Generally, chromatography may be performed prior to mass spectrometry; the chromatography may be liquid chromatography, such as high performance liquid chromatography (HPLC).

Liquid chromatography (LC) including high-performance liquid chromatography (HPLC) rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples. But a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described involving the use of HPLC for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000) (manual precipitation of blood samples, followed by manual CIS solid phase extraction, injection into an HPLC for chromatography on a C18 analytical column, and MS/MS analysis).

One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e., mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the dihydroxyvitamin D metabolite of interest prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Research has shown that epimerization of the hydroxyl group of the A-ring of vitamin $D_3$ metabolites is an important aspect of vitamin $D_3$ metabolism and bioactivation, and that depending on the cell types involved, 3-C epimers of vitamin $D_3$ metabolites (e.g., 3-epi-25(OH)$D_3$; 3-epi-24,25(OH)$_2D_3$; and 3-epi-1,25(OH)$_2D_3$) are often major metabolic products. See Kamao et al., J. Biol. Chem., 279:15897-15907 (2004). Kamao et al., further provides methods of separating various vitamin D metabolites, including 3-C epimers, using chiral HPLC. Accordingly, the invention also provides methods of detecting the presence, absence and/or amount of a specific epimer of one or more vitamin D metabolites, preferably vitamin $D_3$ metabolites, in a sample by (1) separating one or more specific vitamin D metabolites by chiral chromatography, preferably chiral HPLC; and (2) detecting the presence and/or amount of one or more vitamin D metabolites using mass spectrometry methods as described herein. The chiral chromatography procedures described in Kamao et al., are suitable for the methods of the invention, however, one of ordinary skill in the art understands that there are numerous other chiral chromatography methods that would also be suitable. In certain embodiments the method includes, separating 25(OH)$D_3$ from 3-epi-25(OH)$D_3$, if present in a sample, using chiral chromatography; and detecting the presence and/or amount of the 25(OH)$D_3$ and the 3-epi-25(OH)$D_3$ in the sample using mass spectrometry. In related embodiments, the method includes separating 1α,25(OH)$_2D_3$ from 3-epi-1α,25 (OH)$_2D_3$, if present in a sample, using chiral chromatography; and detecting the presence and/or amount of the 1α,25 (OH)$_2D_3$ and the 3-epi-1α,25(OH)$_2D_3$ in the sample using mass spectrometry. In certain embodiments of the invention, chiral chromatography is used in conjunction with the HTLC methods described above.

Detection and Quantization by Mass Spectrometry

Disclosed are mass spectrometric methods for detecting the presence or amount of one or more dihydroxyvitamin D metabolites in a sample. In certain aspects the method involves forming an amine/dihydroxyvitamin D metabolite adduct or an alkali metal ion/dihydroxyvitamin D metabolite adduct, ionizing the adduct, detecting the ion(s) by mass spectrometry, and relating the presence or amount of the ion(s) to the presence or amount of the dihydroxyvitamin D metabolite(s) in the sample.

Mass spectrometry may be performed using a mass spectrometer which includes an ion source for ionizing the fractionated sample and creating charged molecules for further analysis. For example ionization of the sample may be performed by electrospray ionization (ESI), atmospheric pressure chemical ionization (APCI), atmospheric pressure photoionization (APPI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). Preferably, the mass-to-charge ratio is determined using a quadropole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS$_n$." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 100 to 2000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain embodiments, an internal standard is used to generate a standard curve for calculating the quantity of the dihydroxyvitamin D metabolite. Methods of generating and using such standard curves are well known in the art and one of ordinary skill is capable of selecting an appropriate internal standard. For example, an isotope of a dihydroxyvitamin D metabolite may be used as an internal standard, in some embodiments the dihydroxyvitamin D metabolite is a deuterated dihydroxyvitamin D metabolite. Numerous other methods for relating the presence or amount of an ion to the presence or amount of the original molecule will be well known to those of ordinary skill in the art.

One or more steps of the methods of the invention can be performed using automated machines. In certain embodiments, one or more purification steps are performed on line, and more preferably all of the purification and mass spectrometry steps may be performed in an on-line fashion.

In certain embodiments, such as MS/MS, where precursor ions are isolated for further fragmentation, collisionally activated dissociation (CAD) is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In certain embodiments dihydroxyvitamin D metabolites are detected and/or quantified using LC-MS/MS as follows. The samples are subjected to liquid chromatography, preferably HPLC, the flow of liquid solvent from the chromatographic column enters the heated nebulizer interface of a LC-MS/MS analyzer and the solvent/analyte mixture is converted to vapor in the heated tubing of the interface. The analytes (i.e., dihydroxyvitamin D metabolites), contained in the nebulized solvent, are ionized by the corona discharge needle of the interface, which applies a large voltage to the nebulized solvent/analyte mixture. The ions, i.e., precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of the specific dihydroxyvitamin D metabolites to be analyzed. Precursor ions with the correct m/z ratios of the precursor ions of specific dihydroxyvitamin D metabolites are allowed to pass into the collision chamber (Q2), while unwanted ions with any other m/z collide with the sides of the quadrupole and are eliminated. Precursor ions entering Q2 collide with neutral Argon gas molecules and fragment. This process is called Collisionally Activated Dissociation (CAD). The fragment ions generated are passed into quadrupole 3 (Q3), where the fragment ions of the desired dihydroxyvitamin D metabolites are selected while other ions are eliminated.

The methods of the invention may involve MS/MS performed in either positive or negative ion mode. Using standard methods well known in the art, one of ordinary skill is capable of identifying one or more fragment ions of a particular precursor ion of a dihydroxyvitamin D metabolite that can be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (vitamin D metabolite) of interest. In certain embodiments, the area under the curves, or amplitude of the peaks, for fragment ion(s) and/or precursor ions are measured to determine the amount of a dihydroxyvitamin D metabolite. As described above, the relative abundance of a given ion can be converted into an absolute amount of the original analyte, i.e., dihydroxyvitamin D metabolite, using calibration standard curves based on peaks of one or more ions of an internal molecular standard.

In certain aspects of the invention, the quantity of various ions is determined by measuring the area under the curve or the amplitude of the peak and a ratio of the quantities of the ions is calculated and monitored (i.e., "daughter ion ratio monitoring"). In certain embodiments of the method, the ratio(s) of the quantity of a precursor ion and the quantity of one or more fragment ions of a dihydroxyvitamin D metabolite can be calculated and compared to the ratio(s) of a molecular standard of the dihydroxyvitamin D metabolite similarly measured. In embodiments where more than one fragment ion of a dihydroxyvitamin D metabolite is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

In certain embodiments of the invention, the presence or absence or amount of two or more dihydroxyvitamin D metabolites in a sample might be detected in a single assay using the above described MS/MS methods.

Selected Methods

One aspect of the invention relates to a method for assessing the amount of a dihydroxyvitamin D metabolite in a sample, comprising the steps of: (a) combining a first sample with a first amount of an amine or an alkali metal salt, thereby forming a second sample comprising non-covalent adducts comprising the amine or alkali metal salt and the dihydroxyvitamin D metabolite; (b) injecting the second sample into a mass spectrometer, thereby generating a plurality of ions from the non-covalent adducts; and (c) detecting and quantifying one or more ions.

In certain embodiments, the present invention relates to any one of the aforementioned methods, wherein said sample comprises a biological fluid.

In certain embodiments, the present invention relates to any one of the aforementioned methods, further comprising the step of adding a second amount of a buffer to the second sample to adjust the pH of the sample to about 1 to about 7. In certain embodiments, the present invention relates to any one of the aforementioned methods, further comprising the step of adding a second amount of a buffer to the second sample to adjust the pH of the sample to about 1 to about 2. In certain embodiments, the present invention relates to any one of the aforementioned methods, further comprising the step of adding a second amount of a buffer to the second sample to adjust the pH of the sample to about 2 to about 3. In certain embodiments, the present invention relates to any one of the aforementioned methods, further comprising the step of adding a second amount of a buffer to the second sample to adjust the pH of the sample to about 3 to about 4. In certain embodiments, the present invention relates to any one of the aforementioned methods, further comprising the step of adding a second amount of a buffer to the second sample to adjust the pH of the sample to about 4 to about 5. In certain embodiments, the present invention relates to any one of the aforementioned methods, further comprising the step of adding a second amount of a buffer to the second sample to adjust the pH of the sample to about 5 to about 6. In certain embodiments, the present invention relates to any one of the aforementioned methods, further comprising the step of adding a second amount of a buffer to the second sample to adjust the pH of the sample to about 6 to about 7.

In certain embodiments, the present invention relates to any one of the aforementioned methods, further comprising the step of assaying the amount of the dihydroxyvitamin D metabolite in the sample.

In certain embodiments, the present invention relates to any one of the aforementioned methods, wherein the performance of steps (a), (b) and (c) takes place in less than about six hours. In certain embodiments, the present invention relates to any one of the aforementioned methods, wherein the performance of steps (a), (b) and (c) takes place in less than about four hours. In certain embodiments, the present invention relates to any one of the aforementioned methods, wherein the performance of steps (a), (b) and (c) takes place in less than about two hours. In certain embodiments, the present invention relates to any one of the aforementioned methods, wherein the performance of steps (a), (b) and (c) takes place in less than about one hour.

In certain embodiments, the present invention relates to any one of the aforementioned methods, wherein the dihydroxyvitamin D metabolite is present in the first sample at a concentration of about 1 pg/mL to about 100 pg/mL. In certain embodiments, the present invention relates to any one of the aforementioned methods, wherein the dihydroxyvitamin D metabolite is present in the first sample at a concentration of about 10 pg/mL to about 60 pg/mL.

In certain embodiments, the present invention relates to any one of the aforementioned methods, wherein the dihydroxyvitamin D metabolite is 1,25-dihydroxyvitamin $D_2$ or 1,25-dihydroxyvitamin $D_3$. In certain embodiments, the present invention relates to any one of the aforementioned methods, wherein the dihydroxyvitamin D metabolite is 1,25-dihydroxyvitamin $D_2$. In certain embodiments, the present invention relates to any one of the aforementioned methods, wherein the dihydroxyvitamin D metabolite is 1,25-dihydroxyvitamin $D_3$.

In certain embodiments, the present invention relates to any one of the aforementioned methods, wherein the non-covalent adducts comprise the amine and the dihydroxyvitamin D metabolite. In certain embodiments, the present invention relates to any one of the aforementioned methods, wherein the amine is an amine of formula I or formula II. In certain embodiments, the present invention relates to any one of the aforementioned methods, wherein the amine is glycine, alanine, serine, arginine, thyroxine, triiodothyronine, diiodothyronine, or iodothyronine.

In certain embodiments, the present invention relates to any one of the aforementioned methods, wherein the non-covalent adducts comprise the alkali metal salt and the dihydroxyvitamin D metabolite. In certain embodiments, the present invention relates to any one of the aforementioned methods, wherein the alkai salt is a sodium, potassium or lithium salt. In certain embodiments, the present invention relates to any one of the aforementioned methods, wherein the alkali metal salt is a sodium salt. In certain embodiments, the present invention relates to any one of the aforementioned methods, wherein the alkali metal salt is a potassium salt. In certain embodiments, the present invention relates to any one of the aforementioned methods, wherein the alkali metal salt is NaCl or KCl.

In certain embodiments, the present invention relates to any one of the aforementioned methods, wherein the alkali metal salt is added in a buffer solution having a pH of about 1 to about 7. In certain embodiments, the present invention relates to any one of the aforementioned methods, wherein the alkali metal salt is added in a buffer solution having a pH of about 1 to about 2. In certain embodiments, the present invention relates to any one of the aforementioned methods, wherein the alkali metal salt is added in a buffer solution having a pH of about 2 to about 3. In certain embodiments, the present invention relates to any one of the aforementioned methods, wherein the alkali metal salt is added in a buffer solution having a pH of about 3 to about 4. In certain embodiments, the present invention relates to any one of the aforementioned methods, wherein the alkali metal salt is added in a buffer solution having a pH of about 4 to about 5. In certain embodiments, the present invention relates to any one of the aforementioned methods, wherein the alkali metal salt is added in a buffer solution having a pH of about 5 to about 6. In certain embodiments, the present invention relates to any one of the aforementioned methods, wherein the alkali metal salt is added in a buffer solution having a pH of about 6 to about 7.

In certain embodiments, the present invention relates to any one of the aforementioned methods, the concentration of alkali metal salt in the buffer solution comprising the alkali metal salt is between about 0.01 nM to about 10 nM. In certain embodiments, the present invention relates to any one of the aforementioned methods, the concentration of alkali metal salt in the buffer solution comprising the alkali metal salt is between about 0.01 nM to about 0.1 nM. In certain embodiments, the present invention relates to any one of the aforementioned methods, the concentration of alkali metal salt in the buffer solution comprising the alkali metal salt is between about 0.1 nM to about 0.5 nM. In certain embodiments, the present invention relates to any one of the aforementioned methods, the concentration of alkali metal salt in the buffer solution comprising the alkali metal salt is between about 0.5 nM to about 1 nM. In certain embodiments, the present invention relates to any one of the aforementioned methods, the concentration of alkali metal salt in the buffer solution comprising the alkali metal salt is between about 1 nM to about 5 nM. In certain embodiments, the present invention relates to any one of the aforementioned methods, the concentration of alkali metal salt in the buffer solution comprising the alkali metal salt is between about 5 nM to about 10 nM. In certain embodiments, the present invention relates to any one of the aforementioned methods, wherein the mass spectrometer is a Quadrupole Time-of-Flight (Q-TOF) mass spectrometer, Ion Trap Time-of-Flight (IT-TOF) mass spectrometer, Time-of-Flight (TOF) mass spectrometer or a triple quadrupole mass spectrometer. In one embodiment the mass spectrometer is a triple quadrupole time-of-flight mass spectrometer.

In certain embodiments, the present invention relates to any one of the aforementioned methods, wherein the ions are precursor ions.

In certain embodiments, the present invention relates to any one of the aforementioned methods, wherein at least one of said ions has a mass/charge ratio of between about 500 and about 1500. In certain embodiments, the present invention relates to any one of the aforementioned methods, wherein at least one of said ions has a mass/charge ratio of about 399.3, about 439.3, about 455.3, about 492.2, about 506.4, about 522.4, about 591.5, about 772.4, about 1066.2, about 1068.2, about 1192.2 or about 1194.1.

In certain embodiments, the present invention relates to any one of the aforementioned methods, wherein at least one of said ions results from the loss of water from a parent ion. In certain embodiments, the present invention relates to any one of the aforementioned methods, wherein at least one of said ions results from the loss of one water from a parent ion. In certain embodiments, the present invention relates to any one of the aforementioned methods, wherein at least one of said ions results from the loss of two waters from a parent ion. In certain embodiments, the present invention relates to any one of the aforementioned methods, wherein at least one of said ions results from the loss of three waters from a parent ion.

Selected Kits

This invention also provides kits for conveniently and effectively assessing the amount of a dihydroxyvitamin D metabolite in a sample. In certain embodiments, the kits comprise, or consist essentially of, a premeasured portion of an amine. In certain embodiments, the kits comprise, or consist essentially of, a premeasured portion of an alkali metal salt. In certain embodiments, the kits comprise, or consist essentially of, a premeasured portion of an alkali metal salt in a buffer. In certain embodiments, the kits may further comprise, or further consist essentially of, a molecular weight standard. In certain embodiments, the pure standard(s) may be a commercially available standard. In a specific embodiment, the internal standard is deuterated 1,25-dihydroxyvitamin $D_3$. In another specific embodiment, the internal standard is deuterated 1,25-dihydroxyvitamin $D_2$.

A kit of the invention may include instructions in any form that are provided in connection with the methods of the invention in such a manner that one of ordinary skill in the art would recognize that the instructions are to be associated with the methods of the invention. For instance, the instructions may relate to the use, modification, mixing, diluting, and/or preparation of the amine/dihydroxyvitamin D metabolite adduct or the alkali metal ion/dihydroxyvitamin D metabolite adduct. In some cases, the instructions may also include instructions for the use of the mass spectrometer. The instructions may be provided in any form recognizable by a user as a suitable vehicle for containing such instructions; for example, written or published, verbal, audible (e.g., telephonic), digital, optical, visual (e.g., videotape, DVD, etc.) or electronic communications (including Internet or web-based communications), provided in any manner.

EXEMPLIFICATION

The invention now being generally described, it will be more readily understood by reference to the following, which is included merely for purposes of illustration of certain aspects and embodiments of the present invention, and is not intended to limit the invention.

Example 1

Quantitative Analysis of 1,25-Dihydroxyvitamin $D_3$ in a Sample Via Formation of an Amine/1,25-Dihyrdoxyvitamin $D_3$ Adduct To about 200 μL of serum is added about 300 μL methanol containing excess amine and an internal standard (e.g., deuterated 1α,25-dihydroxyvitamin $D_3$). The sample is vortexed and spun. The sample is then injected into a Q-TOF mass spectrometer (Agilent) using a small C18 column (20 mm×2 mm I.D., particle size 1.8 μm). Elute with methanol gradient and quantify at the expected molecular ion peaks. For example, for thyroxine ($T_4$), quantify at 1194.1 to 5 decimals or 1192.2 to 5 decimals.

The mass spectrum of adducts of 1,25-dihydroxyvitamin $D_3$ with thyroxine ($T_4$), triiodothyronine ($T_3$), glycine, alainine, arginine, serine, and iodothyronamine were obtained. The adduct molecular ion peaks which were quantified are shown in the table below.

| amine | peak (m/z, amu) |
|---|---|
| glycine | 492.2 |
| alanine | 506.4 |
| serine | 522.4 |
| arginine | 591.5 |
| iodothyronamine | 772.4 |
| triiodothyronine ($T_3$) | 1066.2 or 1068.2 |
| thyroxine ($T_4$) | 1192.2 or 1194.1 |

In addition, it has been found that the peaks corresponding to the loss of the amine and one equivalent of water may also be measured (at a m/z of 399.3278 amu).

Example 2

Quantitative Analysis of 1,25-Dihydroxyvitamin $D_3$ in a Sample Via Formation of an Alkali Metal Ion/1,25-Dihyrdoxyvitamin $D_3$ Adduct To serum is added a buffer containing an alkali metal salt (at about 1 nM) and, optionally, an internal standard (e.g., deuterated 1α,25-dihydroxyvitamin D$_3$). The sample is vortexed and spun. The sample is then injected into a Q-TOF mass spectrometer (Agilent) using a small C18 column (20 mm×2 mm I.D., particle size 1.8 µm). The sample is eluted with methanol and the expected molecular ion peaks are quantified. For example, for sodium, quantify at 439.3 to 5 decimals.

The mass spectrum of adducts of 1,25-dihydroxyvitamin D$_3$ with sodium (m/z of 439.3206 amu) and potassium (m/z of 455.2955 amu) were obtained.

Example 3

Preparation of a Calibration Curve

Figure 3:
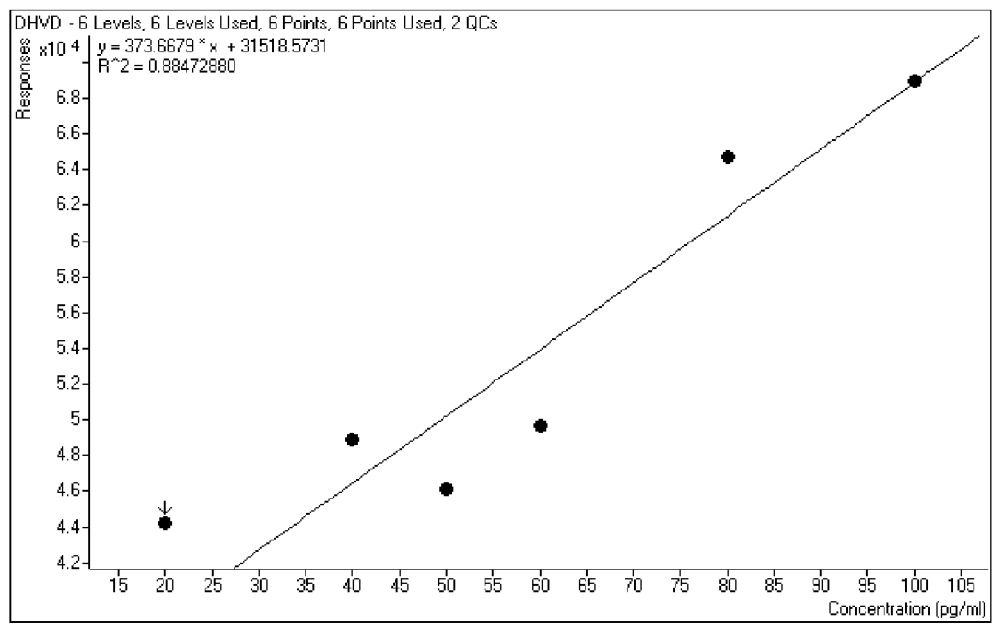
FIG. 3 depicts (top) a calibration curve for 1,25-dihydroxyvitamin $D_3$ (concentration shown on X-axis) with glycine (2 mM glycine); and (bottom) the area under the curve for the 20 pg standard.
Figure 3:
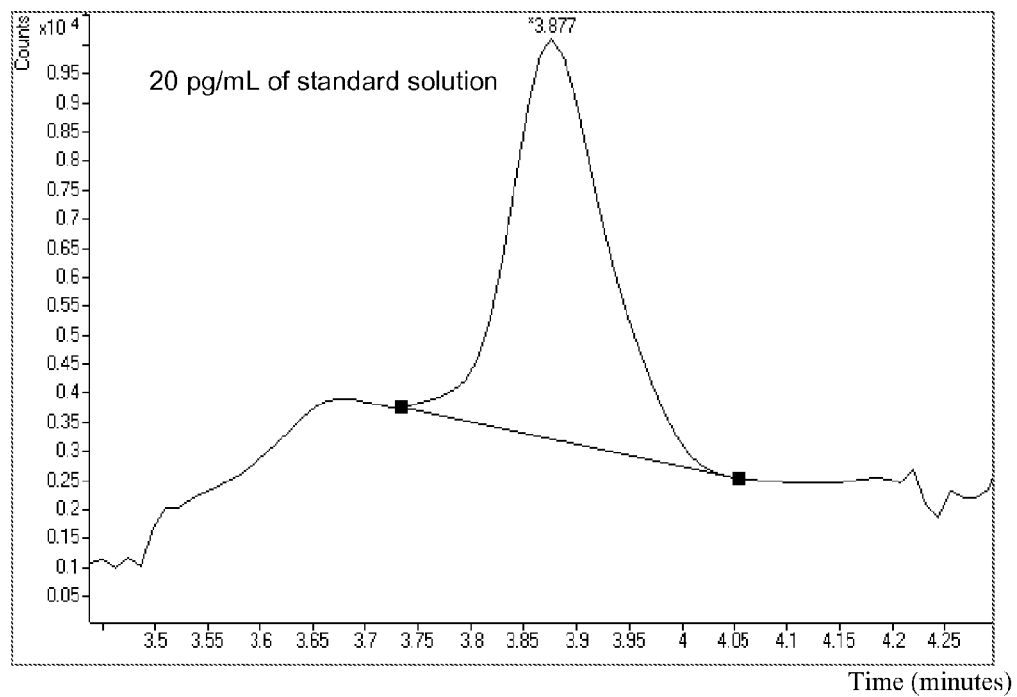

A calibration curve for 1,25-dihydroxyvitamin D$_3$ glycine adducts is shown in FIG. 3. After a standard (18 µL) was injected onto a column (such as an Agilent Sorbex C18 column, 2.1×15 mm, 1.8 micron), the column was washed for about two minutes with a 2% MeOH/2 mM glycine solution. After switching to a 98% MeOH/2 mM glycine solution, the standard was eluted and the area under the curve was measured and correlated to concentration. The flow rate used was 0.35 mL/min. The peak shown in FIG. 3 (bottom) is measured at 492.3610.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method for quantifying the amount of a dihydroxyvitamin D metabolite in a sample, comprising the steps of:
   (a) combining a first sample comprising an amount of dihydroxyvitamin D metabolite with an amine selected from the group consisting of glycine, alanine, serine, arginine, thyroxine, triiodothyronine, diiodothyronine and iodothyronine, thereby forming a second sample comprising non-covalent adducts comprising the dihydroxyvitamin D metabolite and the amine;
   (b) injecting the second sample into a mass spectrometer, thereby generating a plurality of ions from the non-covalent adducts;
   (c) detecting and quantifying one or more of the plurality of ions from the non-covalent adducts; and
   (d) quantifying the amount of the dihydroxyvitamin D metabolite in the first sample,
   wherein the dihydroxyvitamin D metabolite is not derivatized prior to mass spectrometry.

2. The method of claim 1, wherein the non-covalent adducts comprise the amine and the dihydroxyvitamin D metabolite, further comprising the step of adding a buffer to the second sample to adjust the pH of the second sample to about 1 to about 7.

3. The method of claim 1, wherein the performance of steps (a), (b) and (c) takes place in less than about one hour.

4. The method of claim 1, wherein the dihydroxyvitamin D metabolite is present in the first sample at a concentration of about 10 pg/mL to about 60 pg/mL.

5. The method of claim 1, wherein the dihydroxyvitamin D metabolite is 1,25-dihydroxyvitamin D$_2$ or 1,25-dihydroxyvitamin D$_3$.

6. The method of claim 1, wherein the mass spectrometer is a Quadrupole Time-of-Flight (Q-TOF) mass spectrometer, Ion Trap Time-of-Flight (IT-TOF) mass spectrometer, Time-of-Flight (TOF) mass spectrometer or a triple quadrupole mass spectrometer.

7. The method of claim 1, wherein the ions are precursor ions.

8. The method of claim 1, wherein at least one of said ions has a mass/charge ratio of between about 500 and about 1500.

9. The method of claim 1, wherein at least one of said ions has a mass/charge ratio of about 399.3, about 439.3, about 455.3, about 492.2, about 506.4, about 522.4, about 591.5, about 772.4, about 1066.2, about 1068.2, about 1192.2 or about 1194.1.

10. A non-covalent adduct, comprising a dihydroxyvitamin D metabolite and an amine selected from the group consisting of glycine, alanine, serine, arginine, thyroxine, triiodothyronine, diiodothyronine and iodothyronine, wherein the dihydroxyvitamin D metabolite is not derivatized.

11. The adduct of claim 10, wherein the dihydroxyvitamin D metabolite is selected from 1,25-dihydroxyvitamin D$_2$ and 1,25-dihydroxyvitamin D$_3$.

12. A kit for quantifying the amount of a dihydroxyvitamin D metabolite in a sample, consisting essentially of a premeasured portion of an amine selected from the group consisting of glycine, alanine, serine, arginine, thyroxine, triiodothyronine, diiodothyronine and iodothyronine and instructions describing the method of claim 1.

13. The kit of claim 12, further comprising a molecular weight standard.

14. The kit of claim 13, wherein the molecular weight standard is selected from dihydroxyvitamin $D_2$ and dihydroxyvitamin $D_3$.

* * * * *